United States Patent [19]

Botden

[11] 4,457,009
[45] Jun. 26, 1984

[54] DEVICE FOR DETERMINING LOCAL ABSORPTION DIFFERENCES IN AN OBJECT

[75] Inventor: Peter J. M. Botden, Eindhoven, Netherlands

[73] Assignee: U.S. Philips Corporation, New York, N.Y.

[21] Appl. No.: 388,828

[22] Filed: Jun. 16, 1982

Related U.S. Application Data

[63] Continuation of Ser. No. 181,601, Aug. 27, 1980, abandoned.

[30] Foreign Application Priority Data

Sep. 5, 1979 [NL] Netherlands ............... 7906634

[51] Int. Cl.³ ............................................. G03B 41/16
[52] U.S. Cl. ............................................. 378/19; 378/7; 378/147
[58] Field of Search ............................. 378/19, 7, 147

[56] References Cited

U.S. PATENT DOCUMENTS 4,093,863 6/1978 Zacher .................................. 250/445
4,180,737 12/1979 Kengsley .............................. 378/19

Primary Examiner—Craig E. Church
Attorney, Agent, or Firm—Marc D. Schechter

[57] ABSTRACT

The invention relates to a device for determining local absorption differences in a cross-sectional slice of an object. The device comprises an X-ray source and an X-ray detector which is directed toward the X-ray source. The detector comprises a number of plate-shaped collimating elements which are directed toward the X-ray source. On the respective lines of projection of these collimating elements toward the source, there are arranged radiation absorbing elements. The length of each absorbing element, measured in the direction of the X-ray source, is smaller than the length of each collimating element. The width of each absorbing element, measured in a direction at right angles and in the sectional slice, are larger than those of the collimating elements. Apparent variations in the sensitivity of the X-ray detector, due to a lateral shift of the X-ray focus in the X-ray source, are thus substantially mitigated.

1 Claim, 7 Drawing Figures

DEVICE FOR DETERMINING LOCAL ABSORPTION DIFFERENCES IN AN OBJECT

This is a continuation of application Ser. No. 181,601, filed Aug. 27, 1980 now abandoned.

BACKGROUND OF THE INVENTION

The invention relates to a device for determining local absorption differences a cross-sectional slice of in an object. The device comprises an X-ray source for generating a flat, fan-shaped X-ray beam which irradiates the object from different directions during an examination. The device also comprises an X-ray detector which is directed towards the X-ray source and which comprises a plurality of plate-shaped collimating elements which are directed towards the X-ray source. These collimating elements may be accommodated in a separate collimator arranged in front of the detector, or they may be arranged inside the detector.

A form of detector assembly which is often used in computer tomography devices comprises a gas-filled envelope in which a large number of plate-shaped electrodes defined individual ionization chambers. In such a detector assembly, the electrodes may contain a radiation-absorbing material and may even act as a collimating element themselves. Hereinafter, a detector having a separate collimator with a plurality of radiation absorbing collimator plates which are directed toward the X-ray source will be described in detail. However, it is not intended that the general scope of the invention should be restricted to such a detector.

A device of the kind described above is particularly suitable for medical X-ray diagnostics. During an examination, a sectional region of the body of a patient is irradiated from different directions by means of the flat, fan-shaped X-ray beam; locally transmitted radiation is measured. From the measurement data thus obtained, a computer calculates the density distribution in the body section of the patient situated in the irradiated region. This distribution is subsequently displayed, for example, on a television monitor.

In U.S. Pat. No. 4,051,379, a device is described in which an X-ray source, an X-ray detector, and a scattered radiation collimator are all rigidly connected to a rotatable support. The support has a central aperture for accommodating an object to be examined. The X-ray source is arranged on one side of the central aperture, and the X-ray detector and the scattered radiation collimator are arranged on the other side thereof.

During an examination, the rotatable support is rotated about the central aperture so that an object arranged in the aperture is irradiated from different directions. Radiation transmitted by the object is measured by means of the X-ray detector. The detector comprises a large number of individual elemental ionization chambers which are arranged on an arc of a circle and which are defined by plate-shaped electrodes which are directed towards the X-ray source. Collimator plates of the scattered radiation collimator are arranged along the respective lines of projection, of the plate-shaped electrodes towards the X-ray source. The collimator plates are thus directed, like the electrodes, toward the X-ray source.

In U.S. Pat. No. 4,093,863, a device is described in which an X-ray source, an X-ray detector, and a scattered radiation collimator are not rigidly connected to a single rotatable support. Instead, the X-ray source is mounted on a first rotatable support, while the X-ray detector and the scattered radiation collimator are mounted on a second rotatable support.

The X-ray detector in this device comprises a closed array of ionization chambers which are arranged along part of the circumference of a circle. The chambers are defined by plate-shaped electrodes which are directed towards the center of the circle. The rotatable supports are linked so that the center of the circle always coincides with the X-ray source during an examination. Collimator plates are arranged to extend along the respective lines of projection of the plate-shaped electrodes toward the source, so that they are directed, like the electrodes, toward the X-ray source.

A drawback of the known devices described above is that an apparent change in the sensitivity of the detector is liable to occur during an examination, thus introducing measurement errors which give rise to disturbing errors in the calculation of the density distribution of the examined section of the object. When an X-ray source in the form of, for example, a rotary anode X-ray tube is made, the location within the X-ray tube at which X-rays are generated (the X-ray focus) will change with respect to the envelope of the X-ray tube during an examination. This occurs because the mean temperature of the rotary anode may become as high as approximately 1500° C. during an examination. An examination may have a duration of up to 30 seconds, and the shape and dimensions of the rotary anode and of the support thereof can change due to thermal expansion during this time. Vibration can also cause movement of the X-ray focus in an X-ray source.

Due to the movement of the X-ray focus in the X-ray source, a varying amount of radiation will be passed by the collimator via the space between adjacent collimator plates. This is because the collimator plates of the scattered radiation collimator are directed towards a predetermined location of the X-ray source. Accordingly, an apparent change will occur in the sensitivity of the detector situated behind the collimator.

SUMMARY OF THE INVENTION

It is an object of the invention to provide an X-ray diagnostic device in which displacement of the X-ray focus in the X-ray source leads to a smaller apparent change in the detector sensitivity. To achieve this, a device according to the invention includes radiation absorbing elements at right angles to the plane of the flat, fan-shaped X-ray beam and along lines of projection of each collimating element towards the X-ray source. The length of each radiation absorbing element, measured in the direction of propagation of the X-rays from the X-ray source, is less than that of the collimating element. The width of each element, measured in a direction transverse to the propagation direction and in the plane of the fan-shaped radiation beam, is greater than that of the collimating element.

The amount of radiation passing between adjacent collimating elements is thus determined by the gap between adjacent absorbing elements arranged in front of the corresponding collimating elements. Because the dimension of the absorbing elements measured in the direction of the X-ray source is less than the corresponding length of the collimating elements, the amount of radiation passing between adjacent collimating elements will change much less in relation to movements of the X-ray focus in the X-ray source. Consequently, changes in the apparent sensitivity of the X-ray detector arranged behind the collimator will also be reduced.

DESCRIPTION OF THE PREFERRED EMBODIMENTS

Figure 1:
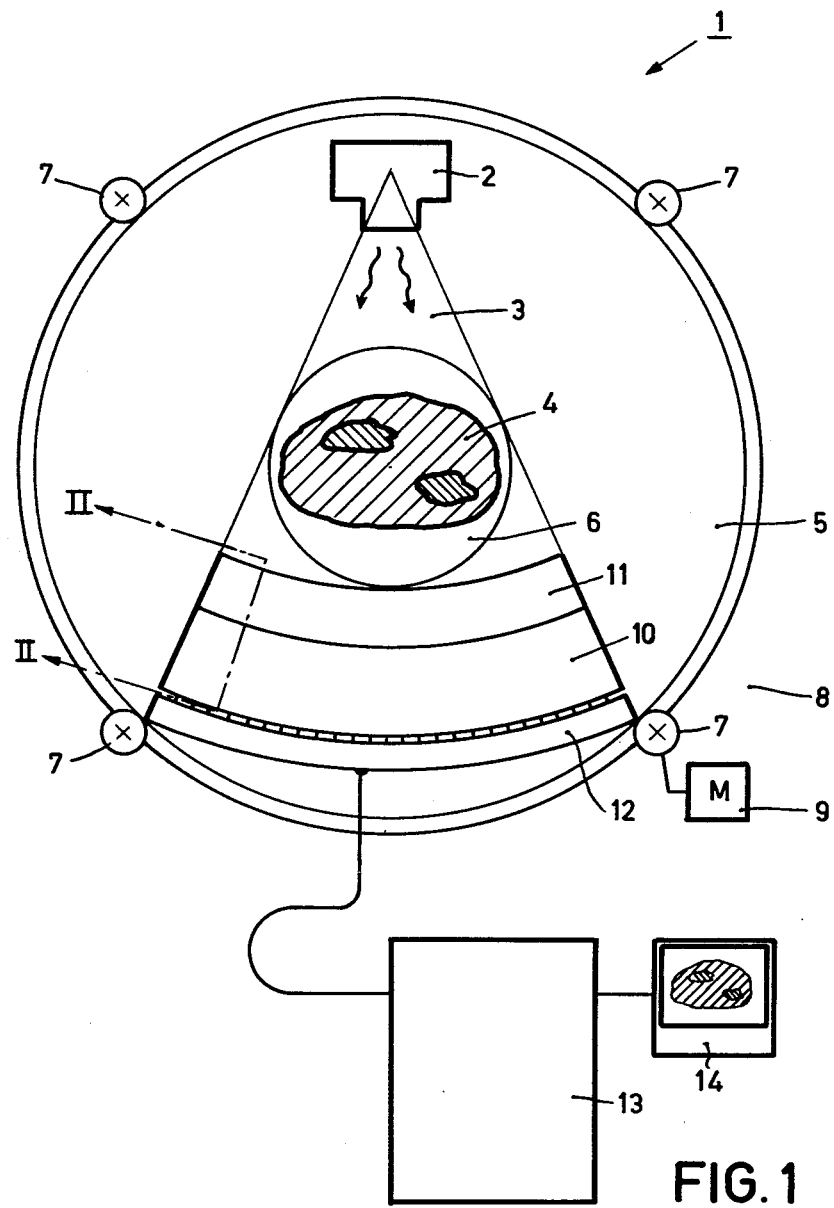
FIG. 1 is a schematic representation of a device for determining local absorption differences in an object.

FIG. 1 schematically shows a device 1 for determining local absorption differences in an object section. The device comprises an X-ray source 2 for generating a flat, fan-shaped X-ray beam 3. An object 4 is irradiated by beam 3 from different directions during an examination. To achieve this, the X-ray source 2 is mounted on a rotatable support 5 which has a central aperture 6 for accommodating the object 4. Support 5 is rotatably journalled in a frame 8 on wheels 7. During an examination, the support 5 is rotated about the central aperture 6 by means of a motor 9.

On the support 5 is X-ray detector 10 and scattered radiation collimator 11. Detector 10 and collimator 11 are mounted so as to be always be directed toward the X-ray source. Radiation collimator 11 is connected to the X-ray detector. The X-ray detector 10 measures radiation transmitted by the object in the various directions; the scattered radiation collimator 11 prevents radiation which is scattered by the object—and which could have an adverse effect on the accuracy of the detector measurement signals—from reaching the X-ray detector 10.

X-ray detector 10 is connected to a signal processing circuit 12 in which detector output signals are processed to form computer input signals. Subsequently, the computer 13 calculates the density distribution in the object section 4 during an distribution is displayed on a television monitor 14 in order to be studied.

Figure 2:
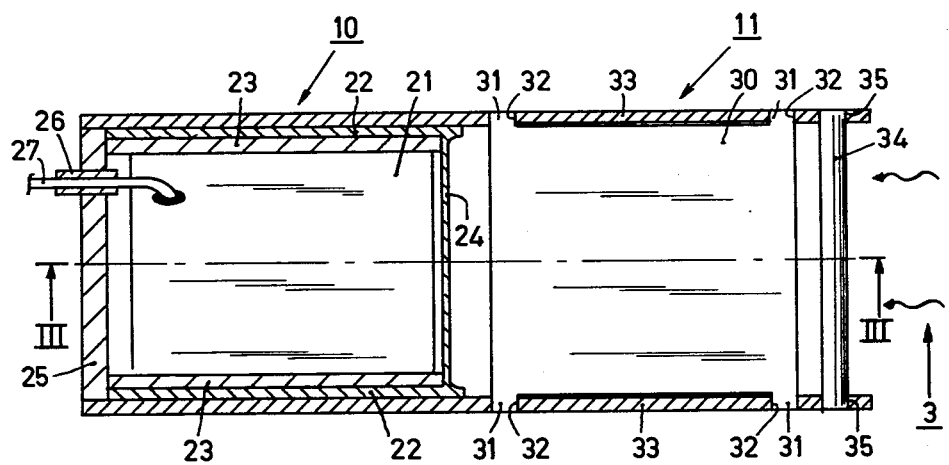
FIG. 2 is a sectional view taken along the line II—II in FIG. 1.
Figure 3:
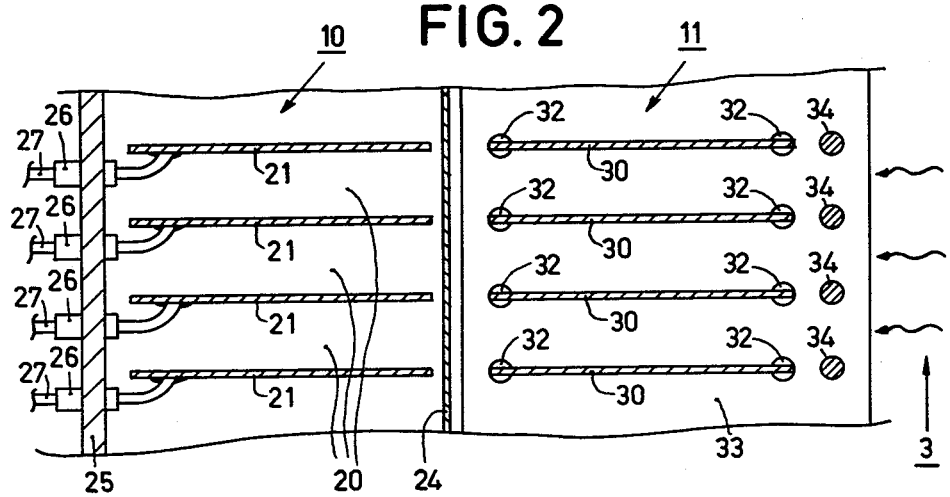
FIG. 3 is a sectional view taken along the line III—III in FIG. 2.

FIGS. 2 and 3 are two different sectional views of the X-ray detector 10 and the scattered radiation collimator 11. The X-ray detector array 10 comprises an array of individual ionization chamber detectors 20 which are arranged along an arc of a circle. Chambers 20 are individually defined and separated by plate-shaped electrodes 21 which form the side walls of each chamber and which are directed toward the X-ray source 2 in FIG. 1. Because the circle has a large radius in comparison with the dimensions of the electrodes 21, the curvature of the X-ray detector 10 is not shown in FIG. 3.

The X-ray detector further comprises a housing 22 in which the electrodes 21 are mounted by means of holders 23 of a synthetic material. The housing 22 comprises an X-ray transmissive wall 24 and a rear wall 25. Connection wires 27 for the electrodes 21 are passed through wall 25 via gastight seals 26.

On a line of projection from each of the electrodes 21 toward the X-ray source, there is arranged a corresponding collimator plate 30 which is also directed toward the X-ray source 2 shown in FIG. 1. Thus, each electrode 21 and its corresponding collimator plate 30 are substantially coplanar. The collimator plates 30 form the scattered radiation collimator 11. Each plate 30 is secured in two mounting plates 33 by means of projections 31, located in holes 32 in plates 33. Plates 33 are connected to the housing 22 of the X-ray detector 10. The collimator plates 30 are made of a material which strongly absorbs X-rays, such as W or Mo. They prevent X-rays scattered by the object 4 (in FIG. 1) from penetrating into the ionization chambers 20.

At right angles to the plane of the flat, fan-shaped X-ray beam 3, and on respective lines of projection through the electrodes 21 and the collimator plates 30 toward the X-ray source, there are arranged X-ray absorbing elements 34. In the direction of propagation of the X-rays 3 to be measured, the lengths of the elements 34 are much less than the lengths of the collimator plates 30. In a direction perpendicular to the collimator plates 30, the widths of elements 34 are much greater than the thicknesses of the collimator plates 30.

For ease and accuracy of manufacture, the elements 34 preferably have a cylindrical shape and are made of W or Mo. The elements 34 are mounted in holes 35 in the mounting plates 33. The mounting plates 33 preferably extend parallel to one another, because the holes 32 and 35 can then be provided in one drilling operation. Then, the collimator plates 30 and the elements 34 can respectively be directed accurately parallel to one another and perpendicularly to the plane of the X-ray beam 3.

Figure 4A:
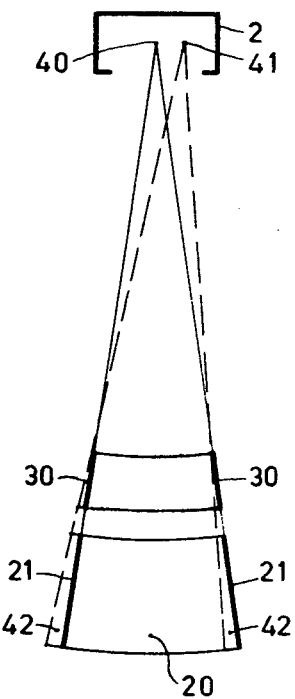
FIGS. 4a and 4b and 5a and 5b illustrate the operation of the device according to the invention.
Figure 4B:
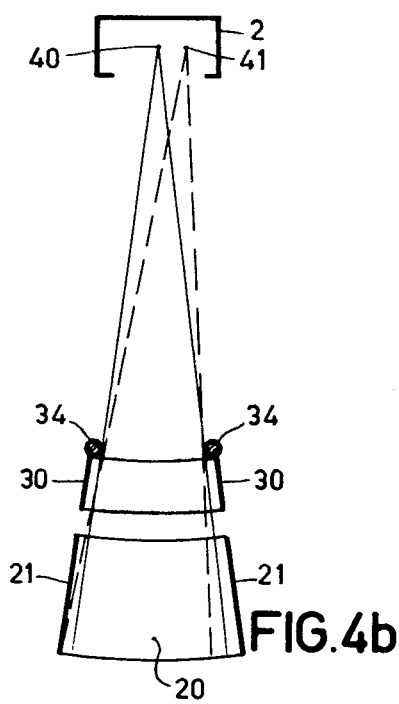

FIGS. 4a and 4b illustrate the operation of the device according to the invention. These Figures show the X-ray source 2, one pair of adjacent electrodes 21, and collimator plates 30. FIG. 4b, one set of adjacent cylindrical elements 34 is also shown. During an examination, which may last up to 30 seconds in practice, the location within the X-ray source 2 at which the X-rays are generated, namely the X-ray focus 40, is liable to shift with respect to the body of the X-ray source 2 and hence also with respect to the electrodes 21 of the detector, the collimator plates 30 and the absorbing elements 34. For example, the focus may shift to the position 41. This shift may be caused not only by thermal expansion within the X-ray source 2, but also, for example, by mechanical vibration.

FIG. 4a shows that, in the absence of the elements 34, a varying quantity of radiation will pass between the collimator plates 30. This variation will be measured in the ionization chamber 20 in response to the shift of the X-ray focus within the X-ray source 2. The collimator plates 30 cast their shadow 42 into the ionization chamber 20.

This problem is solved by using the radiation absorbing elements 34. The amount of radiation which then passes between the adjacent collimator plates 30 will be determined by the gap between the elements 34. Because the length of element 34 in the direction of the corresponding collimator plate 30 is much less than the length of the collimator plate 30, the variation in the amount of radiation passing between the collimator plates 30 in response to the shift of the X-ray focus will be much smaller Thus the apparent change in the sensitivity of the X-ray detector 10, giving rise to disturbing errors in the calculation of the density distribution of the object 4, will thus be substantially mitigated.

Figure 5A:
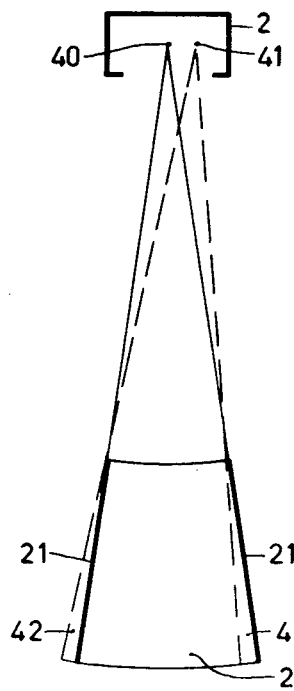
Figure 5B:
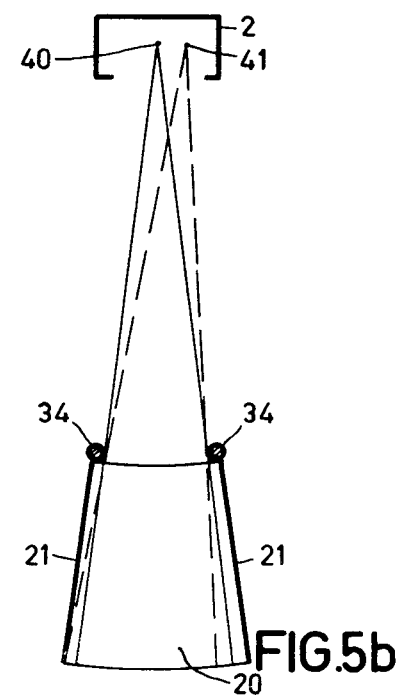

The foregoing description relates to a device 1 comprising a detector 10 with a separate collimator 11 comprising a number of radiation absorbing collimator plates 30 directed towards the X-ray source 2. If the plate-shaped electrodes 21 of the X-ray detector 10 themselves contain a radiation-absorbing material, however, these electrodes 21 themselves will act as a collimating element and the collimator plates 30 can possibly be dispensed with, as shown in FIGS. 5a and 5b. A shift of the X-ray focus within the X-ray source 2 will again cause a varying amount of radiation to be measured, as shown in FIG. 5a. This problem is again solved by using radiation absorbing elements 34 as will be apparent from FIG. 5b.

What is claimed is:

1. A device for determining local absorption differences in a cross-section through an object, said device comprising:

an X-ray source for generating a flat, fan-shaped X-ray beam, said beam irradiating the object from different directions; and an X-ray detector directed toward the X-ray source: characterized in that the X-ray detector comprises:

a plurality of detectors having sidewalls which are directed toward the X-ray source;

a plurality of plate-shaped collimating elements arranged between the detectors and the souce, each collimating element being substantially coplanar with a corresponding sidewall of a detector; and a plurality of radiation absorbing elements, one radiation absorbing element arranged between each collimating element and the X-ray source, each radiation absorbing element having a length in a direction of propagation of the X-ray beam which is less than that of the corresponding collimating element, and each radiation absorbing element having a width in a direction transverse to the propagation direction and in the plane of the fan-shaped beam which is greater than that of the corresponding collimating element.

* * * * *